United States Patent [19]

Nakanishi et al.

[11] Patent Number: 5,624,875
[45] Date of Patent: Apr. 29, 1997

[54] INORGANIC POROUS MATERIAL AND PROCESS FOR MAKING SAME

[75] Inventors: Kazuki Nakanishi, Otsu; Nachiro Soga, Kobe, both of Japan

[73] Assignee: Merck Patent Gesellschaft Mit Beschrankter Haftung, Darmstadt, Germany

[21] Appl. No.: 586,632

[22] PCT Filed: Jul. 15, 1994

[86] PCT No.: PCT/EP94/02331

§ 371 Date: Jan. 18, 1996

§ 102(e) Date: Jan. 18, 1996

[87] PCT Pub. No.: WO95/03256

PCT Pub. Date: Feb. 5, 1995

[30] Foreign Application Priority Data

Jul. 19, 1993 [JP] Japan ..................... 5-200392
Jul. 30, 1993 [JP] Japan ..................... 5-208642

[51] Int. Cl.⁶ .................................... C03C 11/00
[52] U.S. Cl. ................. 501/39; 501/12; 64/17.2; 64/21.4; 64/22
[58] Field of Search .......... 501/12, 39; 65/17.2, 65/21.4, 22

[56] References Cited

U.S. PATENT DOCUMENTS

| 5,009,688 | 4/1991 | Nakanishi | 501/12 |
| 5,100,841 | 3/1992 | Wada et al. | 501/39 |

FOREIGN PATENT DOCUMENTS

| 0363697 | 4/1990 | European Pat. Off. |
| 61-141930 | 6/1986 | Japan. |
| 62-297211 | 12/1987 | Japan. |
| 63-295444 | 12/1988 | Japan. |
| 3285833 | 12/1991 | Japan. |

OTHER PUBLICATIONS

Mori et al, "Synthesis of Spherical Porous Silica Particles", J. Amer. Cer. Soc., vol. 11, pp. 1149–1151 1993 no month.

Chemical Abstracts, vol. 116, No. 2, Abstract No. 10307h.

*Primary Examiner*—Karl Group
*Attorney, Agent, or Firm*—Millen, White, Zelano & Branigan, P.C.

[57] ABSTRACT

A process for producing inorganic porous materials is disclosed. The materials prepared by this process are favorably applied to producing columns for chromatography, porous filters for separating blood, porous catalysts, or enzyme supports. These materials have interconnected continuous macropores with a median diameter larger than 0.1 μm. A preferred embodiment of said materials contains additionally mesopores in the walls of said macropores, said mesopores having a median diameter between 2 and 100 nm.

16 Claims, 3 Drawing Sheets

INORGANIC POROUS MATERIAL AND PROCESS FOR MAKING SAME

BACKGROUND OF THE INVENTION

The present invention is related to a process for producing inorganic porous materials and to materials prepared by such process. These materials are favorably applied to producing columns for chromatography, porous filters for separating blood, porous catalysts, or enzyme supports. Such inorganic porous columns can be favorably applied to liquid- and gas-chromatography. These columns can be used unmodified or modified e.g. by covering their surface with molecules like hydrophobic hydrocarbon ligands (e.g. octadecyl ligands) or like hydrophilic ligands like 2,3-dihydroxypropyl derivatives. The ligands of such modified columns can be further modified using known procedures. Porous catalysts or enzyme supports can be prepared by adding enzymes, e.g. glucose isomerase, or catalytic metal elements, e.g. platinum and palladium. Such inorganic porous columns can also be attached to an injector or a catheter for blood injection.

The sol-gel method is one of liquid phase reaction paths to produce inorganic porous materials, especially silica gels. The sol-gel method denotes widespread processes in which polymerizable low molecular weight species are first generated, and through polymerization reactions, aggregated or polymerized materials are finally obtained. For example, the sol-gel method can be applied by hydrolyzing metal alkoxides, metal chlorides, metal salts or coordinated compounds which typically contain carboxyl or beta-diketone ligands. A process of this kind is disclosed in EP 0 363 697. In this process an organic polymer is used, which is compatible with the solution of the metal alkoxide or its polymer, and which undergoes phase separation during the hydrolysis-polymerization step. The materials produced by this process display connected open pores with a narrow range of the pore size distribution.

In applying porous materials as support or separation devices, the average size and size distribution of pores should be precisely controlled so as to optimize the function of supported substances or the separation efficiency. Accordingly, there have been numerous trials to control the size and distribution of pores by adjusting the reaction parameters of gel preparation. For many applications the porous shaped body should contain defined mesopores in addition to the network of macropores present. Thus the usable inner surface would be enlarged, and distances to be traversed by diffusion minimized.

Typical chromatographic columns widely used are classified into two groups; (a) organic packed column or rod column typically composed of styrene-divinylbenzene copolymers, and (b) inorganic packed column typically composed of silica gel beads.

Organic columns are disadvantageous in the points that: (a) applicable pressure is low due to their low mechanical strength, (b) they swell or shrink on contacting organic solvents, and (c) they cannot be disinfected by heating up to high temperature. Inorganic column materials are free from these disadvantages, and among others silica gels are most widely used.

Conventional inorganic packed columns, however, have some disadvantages different from those of organic columns. That is, columns composed by packing inorganic beads into a cylinder exhibit a high flow resistance and, consequently, the pressure depression is large. As a result, the flow rate decreases and it requires a long time to accomplish the analysis. At the same time, these columns are hard to be used by attaching the injector handled with human hand, because the flow rate becomes so low.

Also, since the sample flow depends on the packing condition, the analysis results tend to scatter when analyzed with several columns with different manufacture lots. Moreover, when the packed columns are attached to an injector or a catheter for blood injection, the packed beads may come out by some accident.

SUMMARY OF THE INVENTION

The present inventors have found that:

(a) Producing a wet bulk gel having phase do mains rich in solvent which converts to macropore spaces larger than 0.1 µm in diameter by the sol-gel method; such domains are usually smaller than 50 µm;

(b) By immersing the bulk gel without crushing or grinding in aqueous solutions with appropriate compositions, the surface of macropores are modified to retain sharply distributed mesopores with a maximum diameter of 100 nm;

(c) As the result, the porous gels thus prepared exhibit dual-pore distributions in macropore and mesopore regions.

When a metalorganic compound having hydrolyzable ligands is hydrolyzed by mixing with an acidic aqueous solution of water-soluble polymer or some other pore-forming phase, the subsequent sol-gel reaction results in the formation of solidified gel in which the phase separated domains one rich in solvent the other rich in silica (gel skeleton, matrix) exist. After the solidification of the solution, the gel is aged for an appropriate period, and then immersed in a matrix dissolving agent, e.g. an aqueous solution having appropriate acid or base concentrations, or an aqueous solution containing fluoride ions. During the immersing process, the substitution of external solution with the solvent-rich phase takes place, allowing the contact of the external solution with the inner-surface of silica-rich phase, i.e., matrix. When the external solution can dissolve the matrix, the inner wall is subjected to a dissolution and re-precipitation process, resulting in the loss of smaller pores and the increase of larger pores. This step is essential for creating the sharply distributed mesopores.

This preferred embodiment of the invention is characterized in that the material contains mesopores in addition to the macropores. Thus its inner surface is increased.

When the matrix is mainly composed of silica, the effect of solvent exchange is very weak in acidic or neutral conditions. With an increase of basicity (or pH value) of the solution, the enlargement of average pore size becomes significant due to the dissolution of the part with small positive radius of curvature and the re-precipitation on the part with small negative radius of curvature.

The present inventors have further found that, different from the packed columns, the porous material of this invention can be used for making rod type monolithic columns with controlled pore size and size distribution which are free from the said disadvantages of conventional inorganic columns.

The present invention has been carried out based on the said findings. The purpose of the invention is to solve various problems with conventional inorganic packed columns, and to supply the new type of column with low flow resistance and high reproducibility which can be easily handled. The object of the present invention is to provide an inorganic porous column, mainly composed of glass or glass-ceramic components, having interconnected continuous macropores with a median diameter larger than 0.1 µm. A preferred embodiment of said column contains additionally mesopores in the walls of said macropores, said mesopores having a median diameter between 2 and 100 nm. It is further preferred to make the columns according to the present invention from silica. In a further preferred embodiment the surface of the pores is modified.

Another object of the invention is the use of said inorganic porous column for the chromatographic separation of a mixture of at least two substances.

A further object of the present invention is a process for producing an inorganic porous column via sol-gel route which includes the steps of:

(a) Dissolving a water-soluble polymer or some other pore forming agent in a medium that promotes the hydrolysis of the metalorganic compound (see step b);

(b) mixing the solution with a metalorganic compound which contains hydrolyzable ligands to promote hydrolysis reaction;

(c) solidifying the mixture through the sol-gel transition;

(d) removing the solution by evaporation drying and heat-treatment;

(e) calcining the gel to form the porous material, wherein a mixture of formamide and a polyalcohol is used as pore forming agent.

A further object of the present invention is a process for producing an inorganic porous column which contains additionally mesopores in the walls of said macropores, said mesopores having the diameter of 2 to 100 nm via sol-gel route; said process includes the steps of:

(a) preparing a gel having three dimensional interconnected phase domains one rich in solvent the other rich in inorganic component in which surface pores are contained;

(b) immersing the gel in a liquid which can dissolve said inorganic component;

(c) removing the liquid by evaporation drying and heat-treatment (d) calcining the gel to form the porous material.

An aqueous ammonia solution or an aqueous solution which contains fluoride ions, is preferably used for step (b) if the inorganic component is silica (silicon dioxide).

DETAILED DESCRIPTION OF THE INVENTION

Figure 1:
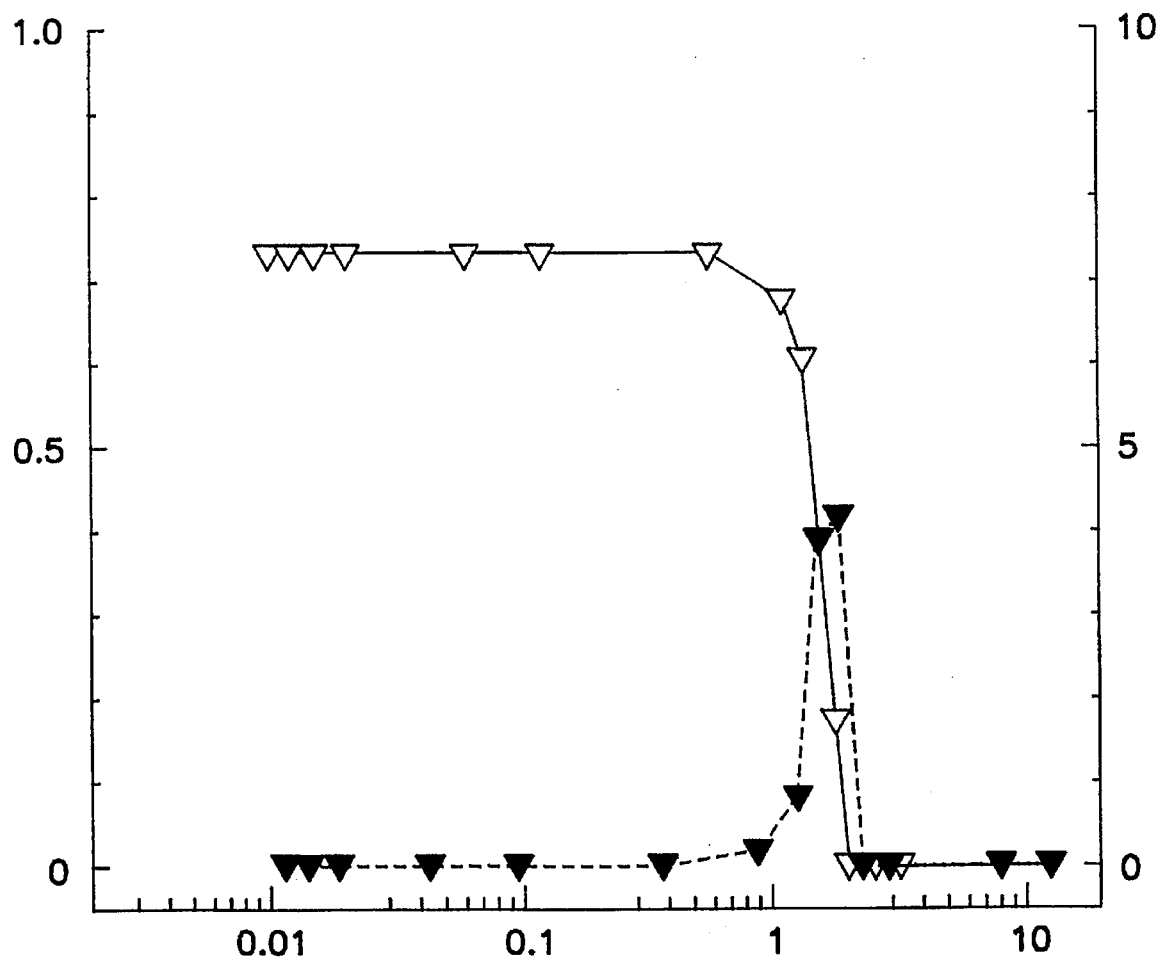
FIG. 1 shows the size distribution curve of the macropore of the porous material obtained in Example 1; the diameter of the macropores (µm, log-scale) is plotted versus the cumulative pore volume ($cm^3/g$; $\nabla$; left ordinate) and the differential pore volume ($cm^3/g$; ▼; right ordinate)

The preferred process according to the present invention is characterized by:

(a) Preparing a gel having 3-dimensional interconnected phase domains one rich in solvent the other rich in inorganic component. The median diameter of said phase domains is not less than 100 nm.

(b) After immersing the gel in a liquid which can dissolve said inorganic component (matrix dissolving agent), removing the liquid by evaporation drying and heat-treatment. In the process, the favorable inorganic component is silica (silicon dioxide) and the favorable matrix dissolving agent is aqueous ammonia solution.

The steps of the above process are:

(1) Dissolving a water-soluble polymer or some other pore forming substance in a medium that promotes the hydrolysis of the metalorganic compound (see step 2);

(2) mixing the solution with a metalorganic compound which has hydrolyzable ligands to promote hydrolysis;

(3) after the solidification of the solution, immersing the solidified product in a matrix dissolving agent;

(4) followed by the evaporation drying and heat-treatment.

In the present invention, the procedure which best fits to the purpose of precise pore size control is the sol-gel method, in which metal alkoxides are used as starting materials with additions of appropriate chemical substances to result in the formation of characteristic phase-separated structure, of which solvent-rich pore forming phase converts to the macropore of the dried gel material. The additive chemical substance has to be chosen so as to work to induce the sol-gel transition of the reacting solution and the phase separation into solvent-rich and silica-rich phases concurrently. Water soluble organic polymers such as poly(ethylene oxide) are favorably used as additive chemical substance in the pore forming phase. However, mixtures of a polyalcohol and formamide can be used instead of organic polymer within the scope of this invention.

In the case of silicon alkoxides as metalorganic compound the hydrolysis is done in an acid medium. Diluted organic or inorganic acids are preferred in this case. Especially preferred is the use of acetic acid or nitric acid using concentrations between 1 mmol/l and 2 mol/l. Other acidic media suitable to carry out the hydrolysis of silicon alkoxides are known in the art. Suitable reagents for the hydrolysis of other metalorganic compounds are known in the art as well.

In the case of ordinary gels which have no macropores but three-dimensionally restricted fine pores, the limited diffusive flow of the external solution kinetically prevent the structural evolution, so that the original pore structure considerably remains in the modified pore structure with the solvent exchange. On the other hand, in the case of gels with solvent-rich domains which are converted to macropores after drying, a large fraction of fine pores are restricted only two-dimensionally, which allows a rapid and frequent contact of external solution with the fine pore structure. The fine pores can be completely eliminated parallel to the development of larger pores within a reasonable solvent exchange duration, and the resultant pore size distribution does not exhibit a significant broadening. In addition, in the solvent exchange process, it is better to renew the external solvent for several times in order to enhance the dissolution-reprecipitation process to approach a steady state pore structure.

If silica is used as material for the matrix, the composition of the external solution used in the solvent exchange process is favorably a basic substances such as ammonia or sodium hydroxide. However, as described in the following examples, since the important requirement to the solution is its pH value, other basic substances can be used without problem as well. In addition, among acidic or neutral substances, those having ability to dissolve silica such as hydrofluoric acid can be used as well. For other materials used as matrix appropriate agents to dissolve such material are known in the art; these agents are summarized as matrix dissolving agents.

The time at which the dissolution and re-precipitation reaction reaches the steady state and resulting in the steady-state pore structure depends on the size and volume fraction of macropores as well as on the whole volume of the gel specimen. In order to improve the productivity, it is important to determine the minimum time required to obtain the steady state structure under a given condition.

After finishing the solvent exchange process, the wet gel specimen is subjected to evaporation drying, accompanied by the shrinkage, and becomes the xerogel (dried gel). There tend to remain non-volatile compounds in the xerogel, additional heat-treatment to decompose organic substances are recommended to obtain an aimed inorganic porous material.

To manufacture inorganic porous column, mainly composed of glass or glass-ceramic components, having both interconnected continuous macropores larger than 0.1 µm in diameter and mesopores on the walls of said macropores, the mesopores having the diameter of 2 to 100 nm, in which the total pore volume of the column does not exceed 10 m$^3$/t, the volume ratio of macropores to the total pore is between 20 and 90%, favorably between 50 and 80%, and the volume ratio of mesopores to the total pore exceeds 10%, favorably exceeds 50%. The main component of glass or glass-ceramics is favorably silica (silicon dioxide).

The inorganic porous column can be, for example, produced by hydrolyzing silicon alkoxide under acidic condition in the presence of a pore forming phase, e.g. an aqueous solution of an organic polymer, to obtain a porous gel body, and subsequently removing the pore forming substance and firing the gel.

The organic polymers which can be used as part of the pore forming phase in producing the porous material according to the invention are desired to have considerable solubility in water and water-alcohol mixed solvents. They have to be uniformly dissolved in the solvent mixture generated during the hydrolysis reaction of silicon alkoxide. Polymeric salts such as poly(sodium styrenesulfonate) or poly (potassium styrenesulfonate), polymeric acids which may dissociate to become polyanion such as poly(acrylic acid), polymeric bases which may dissociate to become polycation such as poly(allylamine) or poly(ethyleneimine), non-ionic polymers having ether oxygen in the main chain such as poly( ethylene oxide ), non-ionic polymers having lactone units in the side chain such as poly(vinylpyrrolidone) are suitable examples.

Mixtures containing formamide and a polyalcohol like ethylenglycol, glycerol, or sorbitol can also be used as components of the pore forming phase, glycerol gives the best result among these polyalcohols.

Silicon alkoxides which are desirable in the preparation of the gel are, tetramethoxysilane, tetraethoxysilane and polymerized derivatives of these compounds.

In order to control the pore size and volume fraction of the mesopores, it is desired that the solidified gel body should be immersed in a gel dissolving agent, e.g. an aqueous ammonia solution, before the drying procedure. Depending of the desired size of the mesopores the concentration of the aqueous ammonia is between 10 mmol/l and 10 mol/l. The use of 0.1–1 mol/l aqueous ammonia is preferred.

The inorganic porous column is characterized by precisely controlled sizes and volumes of interconnected macropores and of mesopores formed on the wall of macropores. The proportion of volumes of macropores and mesopores against the total pore volume should be also optimized. The structure of the column depends on the process parameters such as starting composition, reaction temperature, pH and the kind of catalyst, the amount and molecular weight of organic polymer. Therefore, although it is hard to describe the control method of column structure in a simple way, when the above process parameters are fixed, the products exhibit highly reproducible structures.

Although the organic polymer can be removed to a certain degree from the porous gel by washing or exchanging external solvent prior to drying, it is desirable to heat the gel after the washing procedure up to a temperature high enough to thermally decompose the organic polymer to accomplish a complete removal of it.

It should be noted that, since the present inorganic porous column owes its performance mainly to the pore structure, the manufacturing condition is not limited to the examples described below. The porous material produced by the process of this invention can not only be used as rod-like columns but also as other shaped bodies, e.g. filters.

The columns of the present invention can be used for chromatographic separations. Besides this use such columns can be used as support for other purposes, e.g. as bioreactor carrying enzymes, or as support for catalysts, or as support in a (bio)sensor device. It is conceivable that the shape of the porous material is different from that of the columns which are typically rod shaped. An example of such a different shape is a flat sheet, usable for e.g. thin layer chromatography or as support in a (bio)reactor or a (bio)sensor.

Principles of Action

The sample liquid comes into the column from one end, flows through the 3- dimensionally interconnected pores, and goes out of the other end. There exist fewer narrow channels than in the case of conventional packed column, and because of high macropore volume typically exceeding 50 vol-%, the flow resistance becomes very low. As a result the pressure depression between the entrance and exit ends becomes low.

The interconnected macropores present in the porous materials according to the present invention exhibit median diameters ranging from 0.1 to 50 µm; a preferred range for the median diameters of said macropores is from 0.2 to 20 µm, and especially preferred is a range from 0.2 to 10 µm If the size of macropore is constant, the higher macropore volume is the more favorable for the lower pressure depression, however, when the macropore volume exceeds 90%, the mechanical strength of the column becomes so low that the monolithic column cannot be handled to be set into the connecting devices. On the other hand, when the macropore volume is lower than 20%, the pressure depression may become larger than that of the conventional packed column. The favorable macropore volume for chromatographic application is located between 50 and 80%.

The inorganic porous column retains high specific surface area because there exist the mesopores on the walls of macropores. Accordingly, when the functional organic ligands such as octadecyl groups are chemically bonded to the pore surface, or when enzymes such as glucose isomerase or catalyst metals such as platinum and palladium are supported in the pores. the flowing samples contact these functional ligands or molecules or atoms efficiently. Further. the functional ligands supported on mesopores will not be removed by the application of higher flow rate.

The mesopores present in the walls of said macropores exhibit median diameters ranging from 2 to 100 nm; a preferred range for the median diameters of said mesopores is from 2 to 50 nm. and especially preferred is a range from 5 to 30 nm.

The ratio of the mesopore volume to the total pore volume is desired to be more than 10%. If the volume ratio of the mesopore is lower than 10%. even with very high macropore volume fraction of 90%. there exist limited amount of sites available to support the functional ligands. On the other hand. if the total pore volume of pores exceeds 10 m$^3$/t, the mechanical strength of the gel material becomes so low. it becomes difficult to constitute column device with the gel. For the chromatographic applications, the favorable minima of volume for the mesopores are: a volume ratio against the total pore volume higher than 50% and a total specific volume of the mesopores exceeding 1 m$^3$/t.

In addition, even if the ratio of macropore volume against the whole column volume and the specific volume of the mesopore exceeds the above favorable values within the ranges claimed in the present invention, the gel material can be applied to chromatographic operations by combining with appropriate column design which provides mechanical support to the brittle gel piece.

Various process parameters can be used to control the diameter of the macropores:

(a) Increasing the amount of metalorganic compound results in larger pores;

(b) Addition of a lower alkyl alcohol, e.g. methanol or ethanol, results in smaller pores;

(c) changes of the concentration of the pore forming agent (water soluble polymer or formamide and polyol) result in changes of the diameter of the macropores: in the case of neutral polymers capable of forming hydrogen bonds an increase of the concentration of the polymer results in smaller pores and vice versa, whereas in the case of ionic polymers like poly(acrylic acid), or poly(sodium styrenesulfonate), an increase of the concentration of polymer results in larger pores and vice versa.

The diameter of the macropores can further be influenced by the temperature during the gelation process. Details about these process parameters can be seen from the examples.

The diameter of the mesopores is controlled by:

(a) the temperature during the treatment with the matrix dissolving agent; this step is done at a temperature between 10 and 80 ° C.; a temperature between 25° and 60° C. is preferred;

(b) the concentration of the matrix dissolving agent. Details about these process parameters can be seen from the examples.

Without further elaboration, it is believed that one skilled in the art can, using the preceding description, utilize the present invention to its fullest extent. The preferred specific embodiments are, therefore, to construed as merely illustrative, and not limitative of the disclosure in any way whatsoever.

The entire disclosures of all applications, patents, and publications cited above and below, and of corresponding applications Japanese JP 5-200 392. filed Jul. 19, 1993, and JP 5-208 642. filed Jul. 30, 1993, are hereby incorporated by reference.

EXAMPLES

Example 1

Firstly, 0.70 g of poly(ethylene oxide) (product No. 85645-2. manufactured by Aldrich. Molecular weight: 10000) was dissolved in a 0.001 mol/l aqueous solution of acetic acid. Then 5 ml of tetramethoxysilane was mixed with this solution under stirring to promote hydrolysis reaction. After a few minutes stirring, the resultant transparent reaction solution was transferred to a sealed container and was kept at 40° C. In a constant temperature tank. The reaction solution solidified after about 40 minutes.

The solidified sample was further aged at the same temperature for several hours, then immersed in 0.1 mol/l aqueous ammonia solution for three days at 40° C. with thoroughly renewing the external solution every day. The pH value of the ammonia solution was about 10. The gel was then dried at 60° C., and heated up to 600° C. with the temperature raising rate of 100° C./h. Thus the porous material composed of amorphous silica was obtained.

It was confirmed by the electron microscopic observation as well as by the mercury porosimetry measurement that, in the porous silica material thus obtained, uniform macropores with a pore size of about 1.6 μm (1600 nm) were present in an interconnected manner. FIG. 1 shows the pore size distribution of this sample. It was also confirmed by the nitrogen adsorption measurement that mesopores with a pore size of about 10 nm were present in the wall of said macropores.

Figure 2:
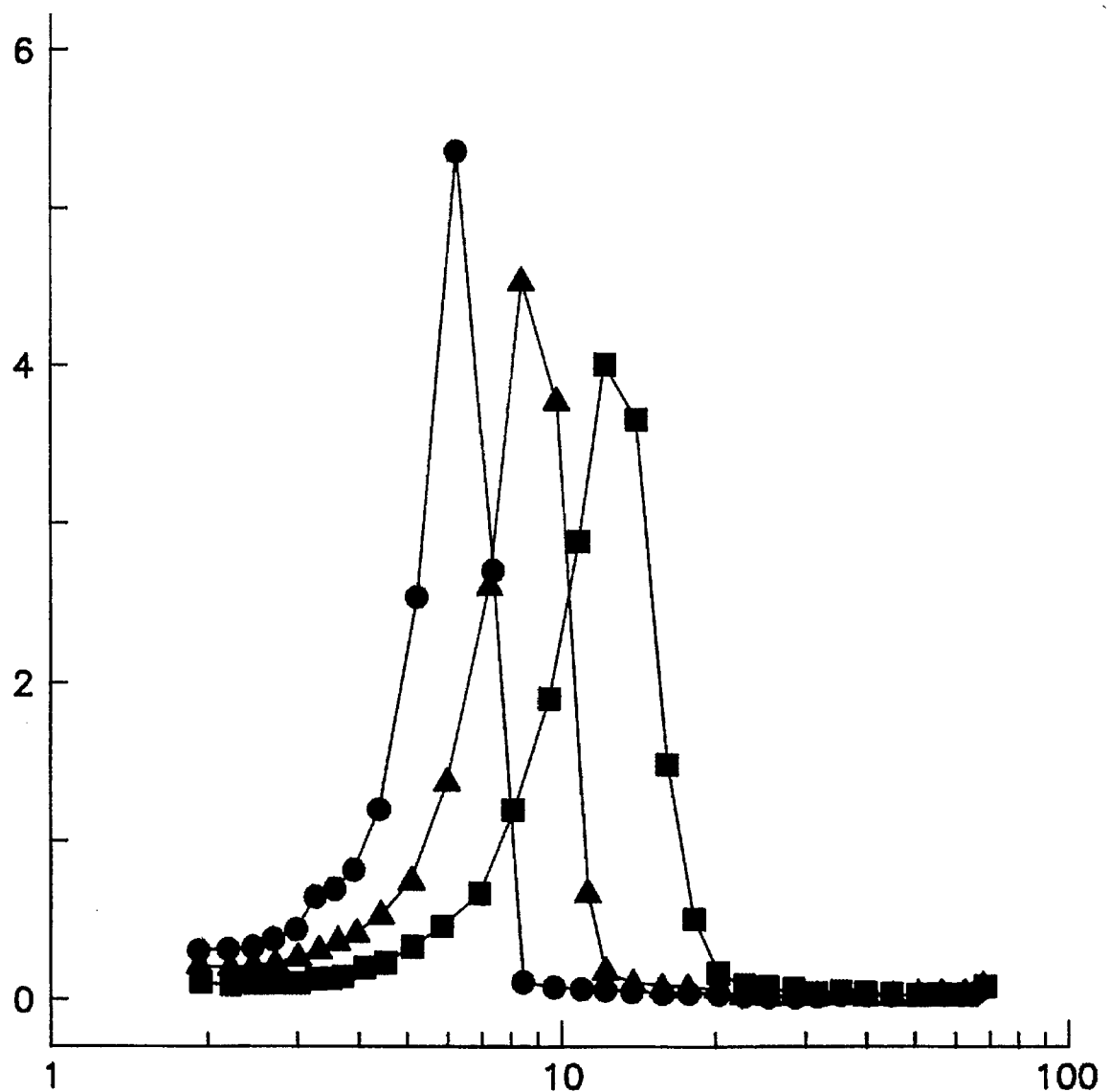
FIG. 2 shows the pore size distribution in nanometer range of the dried and heat-treated gel material after the solvent exchange in 0.1 mol/l aqueous ammonia solution; heat treatment at 25° (●), 40° (▲), and 60° C. (■); the diameter of the mesopores (rim; log-scale) is plotted versus the differential pore volume ($cm^3/g$).

In addition, when the porous materials were manufactured under the same conditions as described above except that the temperature during the solvent exchange with aqueous ammonia solution was varied to 25° C. or 60° C., the distributions of the macropores were not affected, but the median size of mesopores measured by the nitrogen adsorption varied to about 6 nm and 13 nm for 25° C. or 60° C., respectively. FIG. 2 shows the variation of pore size distribution curves with varied temperature of solvent exchange with aqueous ammonia solution. It was confirmed that the higher the temperature of solvent exchange, the larger the median pore size in nanometer-range becomes.

Example 2

The porous materials were manufactured under identical conditions to those described in Example 1 except that the concentration of aqueous ammonia solution used in the solvent exchange process was 1 mol/l with pH value of 10.7.

Figure 3:
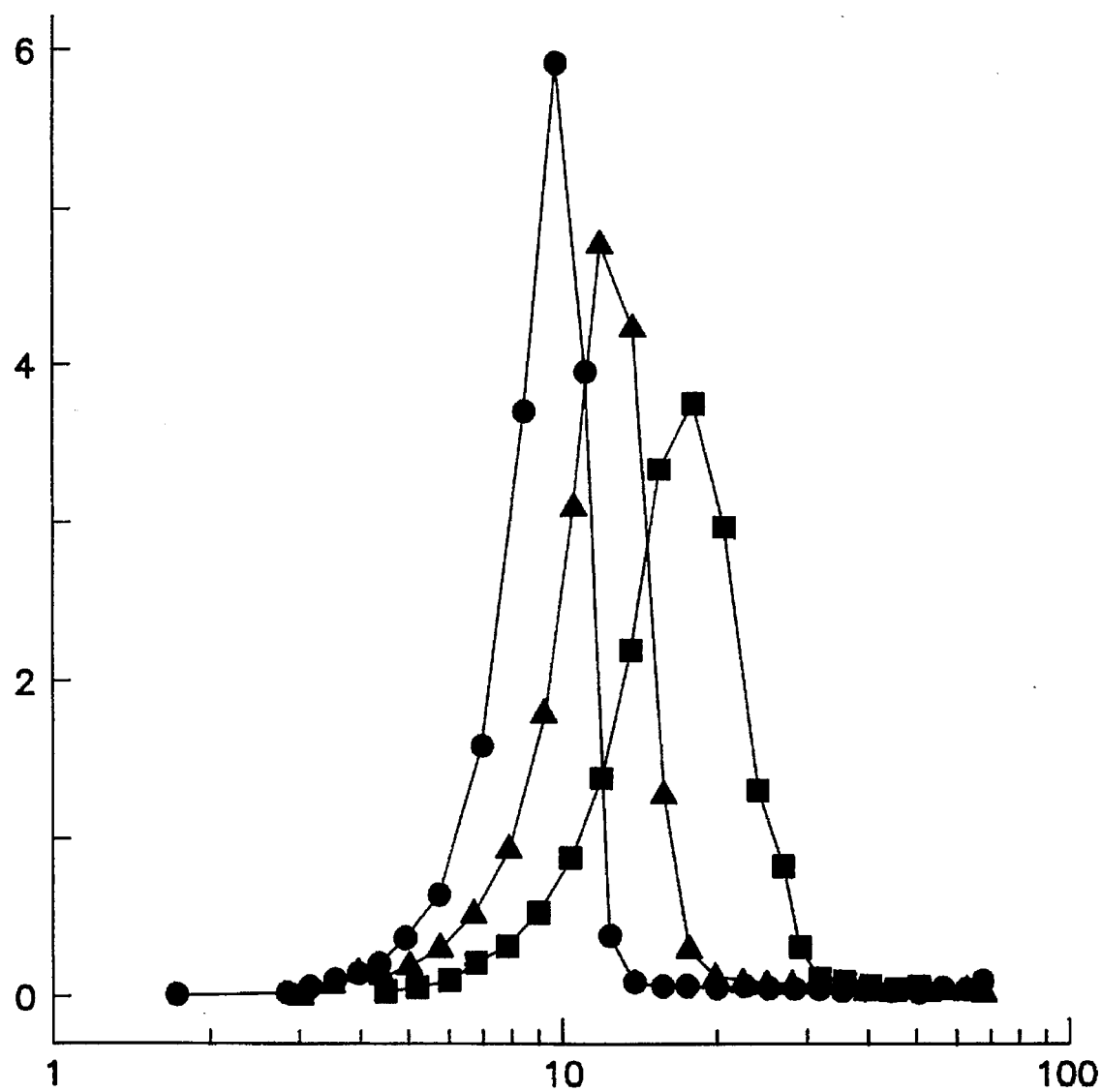
FIG. 3 shows the pore size distribution in nanometer range of the dried and heat-treated gel material after the solvent exchange in 1 mol/l aqueous ammonia solution; heat treatment at 25° (●), 40° (▲), and 60° C. (■); the diameter of the mesopores (nm; log-scale) is plotted versus the differential pore volume ($cm^3/g$). For details see Examples 1 and 2.

The resultant median pore size in nanometer-range at 25°, 40° and 60° C. became 10, 12 and 18 nm, respectively. FIG. 3 shows the variation of pore size distribution curves with varied temperature of solvent exchange with aqueous ammonia solution. It was confirmed that the higher the pH value of external solution, the larger the median pore size in nanometer-range becomes.

Example 3

Firstly, poly(sodium styrenesulfonate) (product No. 24305-1, manufactured by Aldrich) as a metal salt of a polymer, was dissolved in 5.51 g of a 1 mol/l nitric acid aqueous solution to obtain a 20 wt-% solution. Then, 5 ml of tetramethoxysilane was added dropwise thereto over a period of about 1 minute, and the hydrolysis reaction was conducted. After stirring for a few minutes, the resulting transparent solution was transferred to a closed container and maintained in a constant temperature tank at 40° C., whereby it was solidified in about 20 hours.

The solidified sample was further aged for a few days, then immersed in 0.1 mol/l aqueous ammonia solution for 7 days with exchanging the external solution every one day at room temperature. The gel was then dried at 60° C. and heated to 500° C. at a temperature-raising rate of 100° C./hr. The decomposition product of sodium polystyrene sulfonate was washed away with distilled water. Finally the sample was subjected to heat treatment at 800° C. for 2 hours. The gel sample was then mechanically shaped into a rod with the radius of 4.6 mm and the length of 150 mm, thus the porous silica glass column has been obtained.

It was confirmed by the electron microscopic observation as well as by the mercury porosimetry measurement that, in the porous silica glass column thus obtained, uniform pores with a pore size of about 3 μm were present in an interconnected manner. It was also confirmed by the nitrogen adsorption measurement that mesopores with a pore size of about 10 nm were present in the wall of said macropores. The volume and size of macropore of a gel sample dried at 60° C. was almost the same as those of a heat-treated gel sample.

Example 4

A 25 wt% aqueous solution of polyacrylic acid (product No. 19205-8, manufactured by Aldrich, molecular weight: 90000) as a polymer acid, was diluted with distilled water to obtain a 7.4 wt-% aqueous solution. To this solution, concentrated nitric acid was added to obtain a 1 mol/l nitric acid solution. To this solution composed of 0.40 g of polyacrylic acid and 5.51 g of 1 mol/l aqueous nitric acid solution, 7 ml of tetraethoxysilane was added under stirring, and the hydrolysis reaction was conducted. After a few minutes, the resulting transparent solution was transferred to a closed container and maintained in a constant temperature tank at 60° C., whereby it was solidified in about 2 hours.

The solidified sample was further aged for a few hours, and washed by immersing in the mixture of water and ethanol a few times, then immersed in 0.1 mol/l aqueous ammonia solution for 7 days with exchanging the external solution every one day at room temperature. The gel was then dried at 60° C., and was mechanically shaped into a rod with the radius of 4.6 mm and the length of 150 mm.

It was confirmed by the electron microscopic observation as well as by the mercury porosimetry measurement that, in the porous silica glass column thus obtained, uniform pores with a pore size of about 3 μm were present in an interconnected manner. It was also confirmed by the nitrogen adsorption measurement that meso pores with a pore size of about 10 nm were present in the wall of said macropores.

When ethanol was added in an amount of up to 5 ml to the above reaction solution for the solidification, the pore size of the resulting pores body tended to be small, and it was possible to control the pore size continuously to the minimum of about 0.5 μm. Further, by changing the amount of the 1 mol/l nitric acid aqueous solution from the minimum of 3.3 g to the maximum of 16.5 g, it was possible to control the macropore size of the resulting porous body from the maximum of about 10 μm to the minimum of about 0.2 μm. Further, by increasing the amount of the polyacrylic acid and by changing the reaction temperature, the size of macropores could be controlled in a similar way.

The above dried gel sample was heated up to 800° C. with the temperature-raising rate of 100° C./hr and maintained at this temperature for 2 hours. The porous silica glass column having almost the similar macropore structure as the above described dried gel sample has thus been obtained.

Example 5

Firstly, formamide (A) and glycerol (B) was mixed with the molar ratio of 3:2. Then tetramethoxysilane (C) and 1 mol/l aqueous nitric acid solution (D) was mixed with the above mixture in the molar ratio of A:B:C:D=3:2:1:1.5. The mixture was well stirred and homogenized to give transparent reaction mixture. A 10 ml of the reaction mixture was transferred into a sealed cylinder with the inner diameter of 6 mm and the length of 200 mm, and was maintained at 40° C. for solidification. As the result of the hydrolysis and polycondensation reaction, the gel was obtained in a rod shape.

The solidified rod-shaped gel sample was immersed in the 1 mol/l aqueous nitric acid solution at room temperature for one day, then immersed in 0.1 mol/l aqueous ammonia solution for 7 days with exchanging the external solution every one day at room temperature. The gel was then dried at 60° C., and heated up to 700° C. with the temperature-raising rate of 100° C./hr and maintained at this temperature for 2 hours. The porous silica glass column has thus been obtained.

It was confirmed by the electron microscopic observation as well as by the mercury porosimetry measurement that, in the porous silica glass column thus obtained, uniform pores with a pore size of about 3 μm were present in an interconnected manner. It was also confirmed by the nitrogen adsorption measurement that meso pores with a pore size of about 8 nm were present in the wall of said macropores.

Example 6

The following experiments were carried out to demonstrate the relation between microstructure of the column and its performance. The column samples having different microstructures were prepared with the same starting materials as described in Example 3 using varied amounts of tetmmethoxysilane as indicated in table 1.

TABLE 1

| No. | Amount of Tetra-methoxysilane(ml) | Other Additives | Pore Diameter | |
| | | | Macro- (μm) | Meso- (nm) |
| --- | --- | --- | --- | --- |
| 1 | 3 | None | <0.1 | 6 |
| 2 | 4 | None | 1 | 9 |
| 3 | 5 | None | 3 | 10 |
| 4 | 6 | None | 5 | 11 |
| 5 | 10 | Methanol 5 ml | <0.1 | 7 |

The column performance was evaluated by the pressure depression at a constant flow rate of an appropriate mobile phase.

That is, firstly the porous inorganic column was equipped to a liquid chromatograph, then the pressure required to get the flow rate of 1 ml/min at the exit was measured with an intelligent pump which automatically sets the entrance pressure at a given flow rate. Since the exit is freed to the atmosphere, the entrance pressure corresponds to the pressure depression along the column as it is. The mixture of n-hexane (90 vol-%) and isopropyl alcohol (10 vol-%) was used as a mobile phase. Each ten column samples prepared under an identical condition were tested.

The maximum and minimum values of pressure depression was recorded. The results are listed in table 2 with indications of corresponding column microstructure.

TABLE 2

| No. | Volume Fraction (%) | | Mesopore Volume (m³/t) | Pressure Depression (kg/cm²) | |
|---|---|---|---|---|---|
| | Macropore | Mesopore | | Max | Min |
| 1 | 15 | 40 | 0.3 | >100 | >100 |
| 2 | 50 | 52 | 0.5 | 12 | 8 |
| 3 | 60 | 57 | 0.55 | 3.0 | 2.5 |
| 4 | 70 | 63 | 0.60 | 1.5 | 1.0 |
| 5 | 10 | 38 | 0.2 | >100 | >100 |

As shown in table 2, the columns No. 2 to No. 4, which are within the scope of the present invention, exhibited low pressure depression and the scatter of data was considerably small. On the contrary, the columns No. 1 and No. 5, which are out of the scope of the present invention, retained macropores of which volume ratio lower than 20%, consequently the pressure depressions were too large to be precisely measured with the apparatus used.

Example 7

The following experiments were carried out to demonstrate the relation between microstructure of the column and its performance. The column samples having different microstructures were prepared with the same starting materials as described in Example 4 using varied amounts of tetraethoxysilane as indicated in table 3.

The performance was evaluated by the pressure depression in the same way as described in Example 6. The results are listed in table 4 with indications of corresponding column microstructure.

TABLE 3

| No. | Amount of Tetraethoxysilane (ml) | Other Additives | Pore Diameter | |
|---|---|---|---|---|
| | | | Macro- (μm) | Meso- (nm) |
| 6 | 4 | Ethanol 10 ml | <0.1 | 5 |
| 7 | 6 | None | 1.8 | 9.5 |
| 8 | 7 | None | 2.5 | 9.0 |
| 9 | 8 | None | 3.2 | 8.5 |
| 10 | 10 | None | <0.1 | 5 |

TABLE 4

| No. | Volume Fraction (%) | | Mesopore Volume (m³/t) | Pressure Depression (kg/cm²) | |
|---|---|---|---|---|---|
| | Macropore | Mesopore | | Max | Min |
| 6 | 18 | 43 | 0.25 | >100 | >100 |
| 7 | 50 | 55 | 0.53 | 4.2 | 3.7 |
| 8 | 46 | 58 | 0.58 | 3.8 | 3,3 |
| 9 | 40 | 61 | 0.62 | 3.5 | 3,1 |
| 10 | 20 | 45 | 0.20 | >100 | >100 |

As shown in table 4, the columns No. 7 to No. 9, which are within the scope of the present invention, exhibited low pressure depression and the scatter of data was considerably small.

On the contrary, the column No. 6, which is out of the scope of the present invention, retained macropores of which volume ratio lower than 20%, consequently the pressure depression was too large to be precisely measured with the apparatus used. The column No. 10, of which macropore volume was on the border of preferable range claimed in the present invention, exhibited the pressure depression too large to be precisely measured because the average size of macropore was too small.

Example 8

The following experiments were carried out to clarify the relation between microstructure of the column and its performance. The column samples having different microstructures were prepared with the same starting materials as described in Example 5 using varied proportions of starting materials as indicated in table 5.

TABLE 5

| No. | Tetramethoxysilane | Molar Ratio | | | Pore Diameter | |
|---|---|---|---|---|---|---|
| | | Formamide | Glycerol | Water | Macro- (μm) | Meso- (nm) |
| 11 | 1 | 1.0 | 0.67 | 1.5 | <0.1 | 4 |
| 12 | 1 | 2.0 | 1.33 | 1.5 | 0.3 | 9 |
| 13 | 1 | 2.5 | 1.67 | 1.5 | 3.2 | 9.5 |
| 14 | 1 | 3.0 | 2.0 | 1.5 | 8.5 | 11 |
| 15 | 1 | 4.0 | 2.67 | 2.0 | <0.1 | 4.5 |

The performance was evaluated by the pressure depression in the same way as described in Example 6. The results are listed in table 6 with indications of corresponding column microstructure.

As shown in table 6, the columns No. 12 to No. 14, which are within the scope of the present invention, exhibited low pressure depression and the scatter of data was considerably small. The columns No. 11 and No. 15, of which macropore volume were within the scope of present invention, exhibited the pressure depression too large to be precisely measured because their average size of macropore were too small.

TABLE 6

| No. | Volume Fraction (%) | | Mesopore Volume (m³/t) | Pressure Depression (kg/cm²) | |
|---|---|---|---|---|---|
| | Macropore | Mesopore | | Max | Min |
| 11 | 40 | 42 | 0.31 | >100 | >100 |
| 12 | 62 | 35 | 0.52 | 21 | 17 |
| 13 | 68 | 37 | 0.60 | 2.4 | 2.0 |
| 14 | 72 | 37 | 0.67 | 1.2 | 1.0 |
| 15 | 38 | 40 | 0.28 | >100 | >100 |

Example 9

The following experiments were carried out in order to compare the performance of the presently invented column with that of conventional packed beads column.

That is, silica gel beads having the diameter of 10 μm and density of 1.5 g/cm³ were packed into a cylinder with inner diameter of 4.6 mm and length of 150 mm. The packed column was equipped to a liquid chromatograph and subjected to the similar measurement as described in the above Example 6 to 8. As the result, the pressure depression varied from the minimum of 30 kg/cm² to the maximum of 70 kg/cm² showing considerable differences between columns.

Example 10

The following experiments were carried out to evaluate the analysis performance of inorganic columns after the chemical modification of the macropore surface. The mixture of nitrobenzene and toluene was injected into an ordinary mobile phase. The column No. 13 described in Example 8 was chemically modified to retain octadecyl ligand on its pore surface, and was equipped to a liquid chromatograph. The sample mixture was injected into the column under a standard condition. The packed beads column described in Example 9 was similarly modified with octadecyl ligand, equipped to a liquid chromatograph, and was injected the same sample mixture.

Although both the above columns gave reasonable separations between nitrobenzene and toluene, the pressure depression of the column No. 13 was less than 1/10 of that of packed beads column used as a reference.

EFFECT OF THE PRESENT INVENTION

As described so far, according to the present invention, it is possible to manufacture porous materials with controlled pore distribution. These materials are especially useful for rod type monolithic columns, e.g. for chromatography.

Presently invented inorganic porous column has outstanding features as follows; (1) Since the column consists of a monolithic gel rod, it does not suffer from the conventional problems arising from the packing condition, as well as the performance is highly reproducible even with different production lots. (2) Since the volume and size of interconnected macropores are precisely controlled, the pressure depression can be very small. Accordingly, higher flow rate can be achieved with the conventional pump system, resulting in shortened analysis time. Further, since the functional ligand attached to the macropore wall can contact the solute effectively, a required analysis will be accomplished with shorter column length. (3) The monolithic rod is easy to handle when used by attaching to an injector or a catheter for blood injection. (4) Since the flow path of the sample liquid is sharply controlled in size and shape, the distribution and flow conditions of solutes between mobile and stationary phases do not depend on the position in the column.

We claim:

1. An inorganic porous material comprising a glass or glass-ceramic having interconnected continuous macropores with a median diameter larger than 0.1 μm and having mesopores with a median diameter of 2 to 100 nm on the walls of said macropores.

2. The inorganic porous column of claim 1, wherein the glass or glass-ceramic contains silica as the primary component.

3. The inorganic porous column of claim 1, wherein the percentage of macropore volume to total pore volume is from 20–90%.

4. The inorganic porous column of claim 1, wherein the percentage of mesopore volume to total pore volume is more than 10%.

5. The inorganic porous column of claim 1, wherein the percentage of mesopore volume to total pore volume is more than 50%.

6. The inorganic porous material of claim 1 in the form of a column.

7. The inorganic porous material of claim 1 in the form of a flat sheet.

8. The inorganic porous material of claim 1, wherein the macropores have a median diameter of 0.1 to 50 μm.

9. The inorganic porous material of claim 1, wherein the macropores have a median diameter of 0.2 to 20 μm.

10. The inorganic porous material of claim 1, wherein the surface of the macropores mesopores or both are modified by a functional organic ligand, an enzyme or a catalyst metal.

11. The inorganic porous material of claim 1, wherein the median diameter of the mesopores is 2 to 50 nm.

12. A process for chromatographic separation of a mixture of two substances which comprises passing said mixture through the inorganic porous material of claim 1.

13. A process for the preparation of an inorganic porous material comprising a glass or glass-ceramic having interconnected continuous macropores with a median diameter larger than 0.1 μm and having mesopores with a median diameter of 2 to 100 nm in the walls of said macropores, which comprises:

(a) preparing a gel having three dimensional interconnected phase domains, one phase domain being predominantly solvent and another phase domain being predominantly inorganic material with surface pores;

(b) immersing the gel in a liquid capable of dissolving the inorganic material;

(c) removing the liquid by evaporation drying and heat treatment; and (d) calcining the gel to form the inorganic porous material.

14. The process of claim 13, wherein the inorganic material is silica and the liquid is an aqueous ammonia solution.

15. The process of claim 14, wherein the concentration of the aqueous ammonia solution is 10 mmol/l to 10 mol/l.

16. The process of claim 15, wherein the inorganic material is silica and the liquid is an aqueous solution containing fluoride ions.

* * * * *

UNITED STATES PATENT AND TRADEMARK OFFICE
CERTIFICATE OF CORRECTION

PATENT NO. : 5,624,875
DATED : April 29, 1997
INVENTOR(S) : Kazuki NAKANISHI et al.

It is certified that error appears in the above-indentified patent and that said Letters Patent is hereby corrected as shown below:

Title Page:

Item (75), Inventors:

Change "Nachiro" to read -- Naohiro --.

Signed and Sealed this

Ninth Day of June, 1998

Attest:

BRUCE LEHMAN

Attesting Officer

Commissioner of Patents and Trademarks